(12) United States Patent
McKay

(10) Patent No.: US 6,261,586 B1
(45) Date of Patent: *Jul. 17, 2001

(54) BONE GRAFT COMPOSITES AND SPACERS

(75) Inventor: William F. McKay, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/386,560

(22) Filed: Aug. 31, 1999

Related U.S. Application Data

(63) Continuation of application No. 08/873,276, filed on Jun. 11, 1997, now Pat. No. 5,972,368.

(51) Int. Cl.$^7$ .............................. A61F 2/00; A61F 2/28; A61F 2/44

(52) U.S. Cl. .................... 424/423; 424/422; 424/426; 424/548; 424/549; 514/2; 623/16; 606/61; 523/115; 530/840

(58) Field of Search .................... 424/422, 423, 424/426, 548, 549; 514/2; 623/16; 606/61; 523/115; 530/840

(56) References Cited

U.S. PATENT DOCUMENTS

| | | |
|---|---|---|
| 4,294,753 | 10/1981 | Urist ....................... 260/112 |
| 4,314,380 | 2/1982 | Miyata et al. ................ 3/1.9 |
| 4,472,840 * | 9/1984 | Jeffries ....................... 3/1.9 |
| 4,820,305 | 4/1989 | Harms et al. ................ 623/16 |
| 4,877,864 | 10/1989 | Wang et al. ................ 530/324 |
| 4,878,915 | 11/1989 | Brantigan ................... 623/17 |

(List continued on next page.)

FOREIGN PATENT DOCUMENTS

| | | |
|---|---|---|
| 0 321 277 | 6/1989 | (EP) . |
| 0 723 013 A2 | 7/1996 | (EP) . |
| 0 754 466 A2 | 1/1997 | (EP) . |
| WO 86/07265 | 12/1986 | (WO) . |
| WO 93/00432 | 1/1993 | (WO) . |
| WO 94/26892 | 11/1994 | (WO) . |
| WO 94/26893 | 12/1994 | (WO) . |

OTHER PUBLICATIONS

Urist, M.R., et al., "A Chemosterilized Antigen–Extracted Autodigested Alloimmplant for Bone Banks". *Arch. Surg.*, vol. 110, pp. 416–428 (Apr. 1975).

Spector, M., "Anorganic Bovine Bone and Ceramic Analogs of Bone Mineral as Implants to Facilitate Bone Regeneration", *Clinics in Plastic Surgery*, vol. 21, No. 3, pp. 437–444 (Jul., 1994).

Sofamor Danek Laparoscopic Bone Dowel System: Laparoscopic Surgical Procedure, *Laparoscopic Bone Dowel Surgical Technique* (16 pages total).

\*\*Volek–Smith, H. and Urist, M.R., Recombinant Human Bone Morphogenetic Protein (rhBMP) Induced Heterotopic Bone Development In Vivo and In Vitro, *Proc. Soc. Expt. Bio. Med.* 211:265–272 (1996).

*Primary Examiner*—Thurman K. Page
*Assistant Examiner*—Lakshmi Channavajjala
(74) *Attorney, Agent, or Firm*—Woodard, Emhardt, Naughton Moriarty & McNett

(57) ABSTRACT

A bone graft substitute including a composition of natural selectively deactivated bone material which has been processed to remove associated non-collagenous bone proteins, said bone material containing native collagen materials and naturally associated bone minerals and substantially free from native non-collagenous protein, and a therapeutically effective amount to stimulate bone growth of a bone growth factor in a pharmaceutically acceptable carrier in synergistic combination with said bone material. Spacers composed of the bone graft substitute composition methods for using the spacers are also provided.

14 Claims, 6 Drawing Sheets

U.S. PATENT DOCUMENTS

| | | | |
|---|---|---|---|
| 4,882,149 | 11/1989 | Spector | 424/425 |
| 4,961,740 | 10/1990 | Ray et al. | 606/61 |
| 5,013,649 | 5/1991 | Wang et al. | 435/69.1 |
| 5,015,247 | 5/1991 | Michelson | 606/61 |
| 5,026,373 | 6/1991 | Ray et al. | 606/61 |
| 5,044,104 | 9/1991 | Hopperdietzel | 40/642 |
| 5,106,748 | 4/1992 | Wozney et al. | 435/252.3 |
| 5,108,922 | 4/1992 | Wang et al. | 435/240.2 |
| 5,116,738 | 5/1992 | Wang et al. | 435/69.1 |
| 5,147,402 | 9/1992 | Bohler et al. | 623/16 |
| 5,187,076 | 2/1993 | Wozney et al. | 435/69.1 |
| 5,192,327 | 3/1993 | Brantigan | 623/17 |
| 5,366,875 | 11/1994 | Wozney et al. | 435/69.1 |
| 5,417,975 | 5/1995 | Lussi et al. | 424/435 |
| 5,573,771 | 11/1996 | Geistlich et al. | 424/422 |
| 5,585,116 * | 12/1996 | Bonafice et al. | 424/549 |
| 5,709,683 * | 1/1998 | Bagby | 606/69 |

* cited by examiner

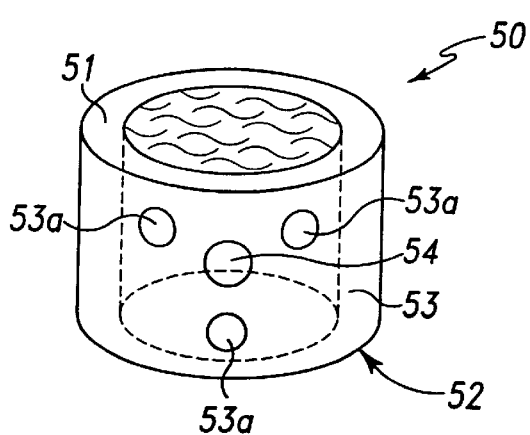
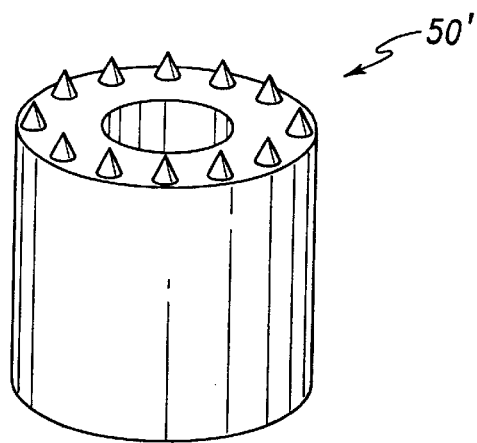
Fig. 7                    Fig. 8
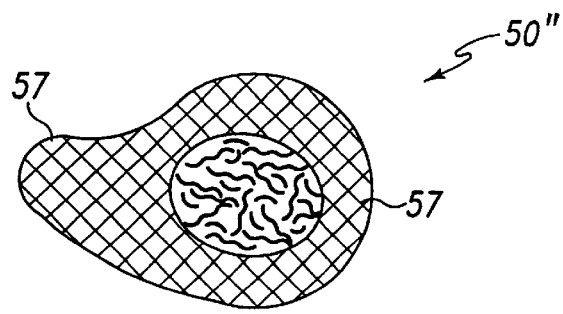
Fig. 9

BONE GRAFT COMPOSITES AND SPACERS

This application is a continuation of applicants' U.S. patent application Ser. No. 08/873,276, filed Jun. 11, 1997, now U.S. Pat. No. 5,972,368.

FIELD OF THE INVENTION

The present invention relates to bone graft substitute materials and spacers composed of the materials for arthrodesis. In specific applications of the invention the materials are provided in synergistic combination with osteogenic compositions.

BACKGROUND OF THE INVENTION

Spinal fusion is indicated to provide stabilization of the spinal column for painful spinal motion and disorders such as structural deformity, traumatic instability, degenerative instability, and post-resection iatrogenic instability. Fusion, or arthrodesis, is achieved by the formation of an osseous bridge between adjacent motion segments. This can be accomplished within the disc space, anteriorly between contiguous vertebral bodies or posteriorly between consecutive transverse processes, laminae or other posterior aspects of the vertebrae.

An osseous bridge, or fusion mass, is biologically produced by the body upon skeletal injury. This normal bone healing response is used by surgeons to induce fusion across abnormal spinal segments by recreating spinal injury conditions along the fusion site and then allowing the bone to heal. A successful fusion requires the presence of osteogenic or osteopotential cells, adequate blood supply, sufficient inflammatory response, and appropriate preparation of local bone. This biological environment is typically provided in a surgical setting by decortication, or removal of the outer, cortical bone to expose the vascular, cancellous bone, and the deposition of an adequate quantity of high quality graft material.

A fusion or arthrodesis procedure is often performed to treat an anomoly involving an intervertebral disc. Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosis. In a healthy, undamaged spine, the annulus fibrosis prevents the nucleus pulposus from protruding outside the disc space.

Spinal discs may be displaced or damaged due to trauma, disease or aging. Disruption of the annulus fibrosis allows the nucleus pulposus to protrude into the vertebral canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Pain relief via discectomy and arthrodesis requires preservation of the disc space and eventual fusion of the affected motion segments.

Bone grafts are often used to fill the intervertebral space to prevent disc space collapse and promote fusion of the adjacent vertebrae across the disc space. In early techniques, bone material was simply disposed between the adjacent vertebrae, typically at the posterior aspect of the vertebrae, and the spinal column was stabilized by way of a plate or rod spanning the affected vertebrae. Once fusion occurred the hardware used to maintain the stability of the segment became superfluous and was a permanent foreign body. Moreover, the surgical procedures necessary to implant a rod or plate to stabilize the level during fusion were frequently lengthy and involved.

It was therefore determined that a more optimal solution to the stabilization of an excised disc space is to fuse the vertebrae between their respective end plates, preferably without the need for anterior or posterior plating. There have been an extensive number of attempts to develop an acceptable intra-discal implant that could be used to replace a damaged disc and maintain the stability of the disc interspace between the adjacent vertebrae, at least until complete arthrodesis is achieved. To be successful the implant must provide temporary support and allow bone ingrowth. Success of the discectomy and fusion procedure requires the development of a contiguous growth of bone to create a solid mass because the implant may not withstand the cyclic compressive spinal loads for the life of the patient.

Many attempts to restore the intervertebral disc space after removal of the disc have relied on metal devices. U.S. Pat. No. 4,878,915 to Brantigan teaches a solid metal plug. U.S. Pat. Nos. 5,044,104; 5,026,373 and 4,961,740 to Ray; 5,015,247 to Michelson and U.S. Pat. No. 4,820,305 to Harms et al., U.S. Pat. No. 5,147,402 to Bohler et al. and 5,192,327 to Brantigan teach hollow metal cage structures. Unfortunately, due to the stiffness of the material, some metal implants may stress shield the bone graft, increasing the time required for fusion or causing the bone graft to resorb inside the cage. Subsidence, or sinking of the device into bone, may also occur when metal implants are implanted between vertebrae if fusion is delayed. Metal devices are also foreign bodies which can never be fully incorporated into the fusion mass.

Various bone grafts and bone graft substitutes have also been used to promote osteogenesis and to avoid the disadvantages of metal implants. Autograft is often preferred because it is osteoinductive. Both allograft and autograft are biological materials which are replaced over time with the patient's own bone, via the process of creeping substitution. Over time a bone graft virtually disappears unlike a metal implant which persists long after its useful life. Stress shielding is avoided because bone grafts have a similar modulus of elasticity as the surrounding bone. Commonly used implant materials have stiffness values far in excess of both cortical and cancellous bone. Titanium alloy has a stiffness value of 114 Gpa and 316L stainless steel has a stiffness of 193 Gpa. Cortical bone, on the other hand, has a stiffness value of about 17 Gpa. Moreover, bone as an implant also allows excellent postoperative imaging because it does not cause scattering like metallic implants on CT or MRI imaging.

Various implants have been constructed from bone or graft substitute materials to fill the intervertebral space after the removal of the disc. For example, the Cloward dowel is a circular graft made by drilling an allogeneic or autogeneic plug from the illium. Cloward dowels are bicortical, having porous cancellous bone between two cortical surfaces. Such dowels have relatively poor biomechanical properties, in particular a low compressive strength. Therefore, the Cloward dowel is not suitable as an intervertebral spacer without internal fixation due to the risk of collapsing prior to fusion under the intense cyclic loads of the spine.

Bone dowels having greater biomechanical properties have been produced and marketed by the University of Florida Tissue Bank, Inc., 1 Progress Boulevard, P.O. Box 31, S. Wing, Alachua, Fla. 32615. Unicortical dowels from allogeneic femoral or tibial condyles are available. The University of Florida has also developed a diaphysial cortical dowel having superior mechanical properties. This dowel also provides the further advantage of having a naturally preformed cavity formed by the existing medullary canal of the donor long bone. The cavity can be packed with osteogenic materials such as bone or bioceramic.

Unfortunately, the use of bone grafts presents several disadvantages. Autograft is available in only limited quantities. The additional surgery also increases the risk of infection and blood loss and may reduce structural integrity at the donor site. Furthermore, some patients complain that the graft harvesting surgery causes more short-term and long-term pain than the fusion surgery.

Allograft material, which is obtained from donors of the same species, is more readily obtained. However, allogeneic bone does not have the osteoinductive potential of autogenous bone and therefore may provide only temporary support. The slow rate of fusion using allografted bone can lead to collapse of the disc space before fusion is accomplished.

Both allograft and autograft present additional difficulties. Graft alone may not provide the stability required to withstand spinal loads. Internal fixation can address this problem but presents its own disadvantages such as the need for more complex surgery as well as the disadvantages of metal fixation devices. Also, the surgeon is often required to repeatedly trim the graft material to obtain the correct size to fill and stabilize the disc space. This trial and error approach increases the length of time required for surgery. Furthermore, the graft material usually has a smooth surface which does not provide a good friction fit between the adjacent vertebrae. Slippage of the graft may cause neural and vascular injury, as well as collapse of the disc space. Even where slippage does not occur, micromotion at the graft/fusion-site interface may disrupt the healing process that is required for fusion.

Several attempts have been made to develop a bone graft substitute which avoids the disadvantages of metal implants and bone grafts while capturing advantages of both. For example Unilab, Inc. markets various spinal implants composed of hydroxyapatite and bovine collagen. In each case developing an implant having the biomechanical properties of metal and the biological properties of bone without the disadvantages of either has been extremely difficult or impossible.

These disadvantages have led to the investigation of bioactive substances that regulate the complex cascade of cellular events of bone repair. Such substances include bone morphogenetic proteins, for use as alternative or adjunctive graft materials. Bone morphogenetic proteins (BMPs), a class of osteoinductive factors from bone matrix, are capable of inducing bone formation when implanted in a fracture or surgical bone site. Recombinantly produced human bone morphogenetic protein-2 (rhBMP-2) has been demonstrated in several animal models to be effective in regenerating bone in skeletal defects. The use of such proteins has led to a need for appropriate carriers and fusion spacer designs.

Due to the need for safer bone graft materials, bone graft substitutes, such as bioceramics, have recently received considerable attention. The challenge has been to develop a bone graft substitute which avoids the disadvantages of metal implants and bone grafts while capturing the advantages of both. Calcium phosphate ceramics are biocompatible and do not present the infectious or immunological concerns of allograft materials. Ceramics may be prepared in any quantity which is a great advantage over autograft bone graft material. Furthermore, bioceramics are osteoconductive, stimulating osteogenesis in boney sites. Bioceramics provide a porous matrix which further encourages new bone growth. Unfortunately, ceramic implants typically lack the strength to support high spinal loads and therefore require separate fixation before the fusion.

Of the calcium phosphate (TCP) ceramics, hydroxyapatite (HA) and tricalcium phosphate ceramics have been most commonly used for bone grafting. Hydroxyapatite is chemically similar to inorganic bone substance and biocompatible with bone. However, it is slowly degraded. β-tricalcium phosphate is rapidly degraded in vivo and is too weak to provide support under the cyclic loads of the spine until fusion occurs. Developing an implant having the biomechanical properties of metal and the biological properties of bone without the disadvantages of either has been extremely difficult or impossible.

It recently became apparent that natural bone mineral is not actually as close to the chemistry and structure of hydroxyapatite as was previously believed. (Spector, 21 Clinics in Plastic Surgery 437–444, 1994, the complete text of which is herein incorporated by reference.) Natural bone mineral contains carbonate ions, magnesium, sodium, hydrogenophosphate ions and trace elements. Bone mineral also has a different crystalline structure than HA. Other details of bone chemistry are disclosed in U.S. Pat. No. 4,882,149 to Spector. Mimicing the chemistry and microstructure of bone is important to obtain a beneficial modulus of elasticity and resorbtion rate.

Several attempts have been made to make materials which are closer to the microstructure of bone. Some disclose removing organic material from bone to yield bone mineral. Some of the materials are used as drug carriers as disclosed in, for example, U.S. Pat. No. 5,417,975. U.S. Pat. No. 4,882,149 to Spector describes a bone mineral material which is free from fat and bone proteins. The result is a powdery, brittle radiopaque material which can be used to deliver bone growth proteins. The Spector mineral is thought to be closer to natural bone mineral than synthetic calcium phosphate ceramics but it does not have characteristics which allow it to be shaped into formed objects. U.S. Pat. Nos. 4,314,380 to Miyata et al. and 5,573,771 disclose adding collagen or gelatin to bone mineral. However, it is unclear how close these materials are to the natural structure of bone because the crystalline structure is disrupted when all of the proteins are removed from the treated bone. Urist et al. (110 Arch Surg 416, 1975) discloses a chemosterilized antigen-extracted autodigested alloimplant which is thought to preserve the morphogenetic potential of the material. None of these materials are thought to yield a non-collagenous-protein-free bone mineral which is identical to natural bone.

A need has remained for fusion spacers which stimulate bone ingrowth and avoid the disadvantages of metal implants yet provide sufficient strength to support the vertebral column until the adjacent vertebrae are fused.

A need has also remained for bone graft substitutes which provide the osteogenic potential and low risk of infectious or immunogenic complications of autograft without the disadvantages of autograft.

SUMMARY OF THE INVENTION

In accordance with one aspect of the invention, bone graft compositions and vertebral spacers composed of bone graft compositions are provided. In one aspect, the invention provides deactivated bone graft compositions in synergistic combination with a bone growth factor.

One object of the invention is to provide a bone graft substitute having the natural mineral structure, nonimmunogenicity, safety and osteoinductive potential of autograft. Another object of the invention is to provide spacers for engagement between vertebrae which restore the intervertebral disc space and supports the vertebral column while encouraging bone ingrowth and avoiding stress shielding.

One benefit of the present invention is that it solves many of the problems associated with the use of bone graft. The deactivation process removes immunogenic and disease causing agents while retaining the natural micro-structure of bone. This feature allows the use of xenograft, which is available in virtually unlimited supply. Fortifying the graft with a bone growth factor makes the graft osteoinductive which makes the pain and risk of harvesting autograft unnecessary. An additional benefit is that the invention provides a stable scaffold for bone ingrowth before fusion occurs. Still another benefit of this invention is that it allows the use of bone grafts without the need for metal cages or internal fixation, due to the increased speed of fusion. Other objects and further benefits of the present invention will become apparent to persons of ordinary skill in the art from the following written description and accompanying Figures.

BRIEF DESCRIPTION OF THE DRAWINGS

FIG. 7 is a selectively deactivated cortical ring packed with an osteogenic material.

FIG. 8 is yet another selectively deactivated cortical ring embodiment provided by this invention.

FIG. 9 is another embodiment of a cortical ring provided by this invention.

DESCRIPTION OF THE PREFERRED EMBODIMENT

Figure 1:
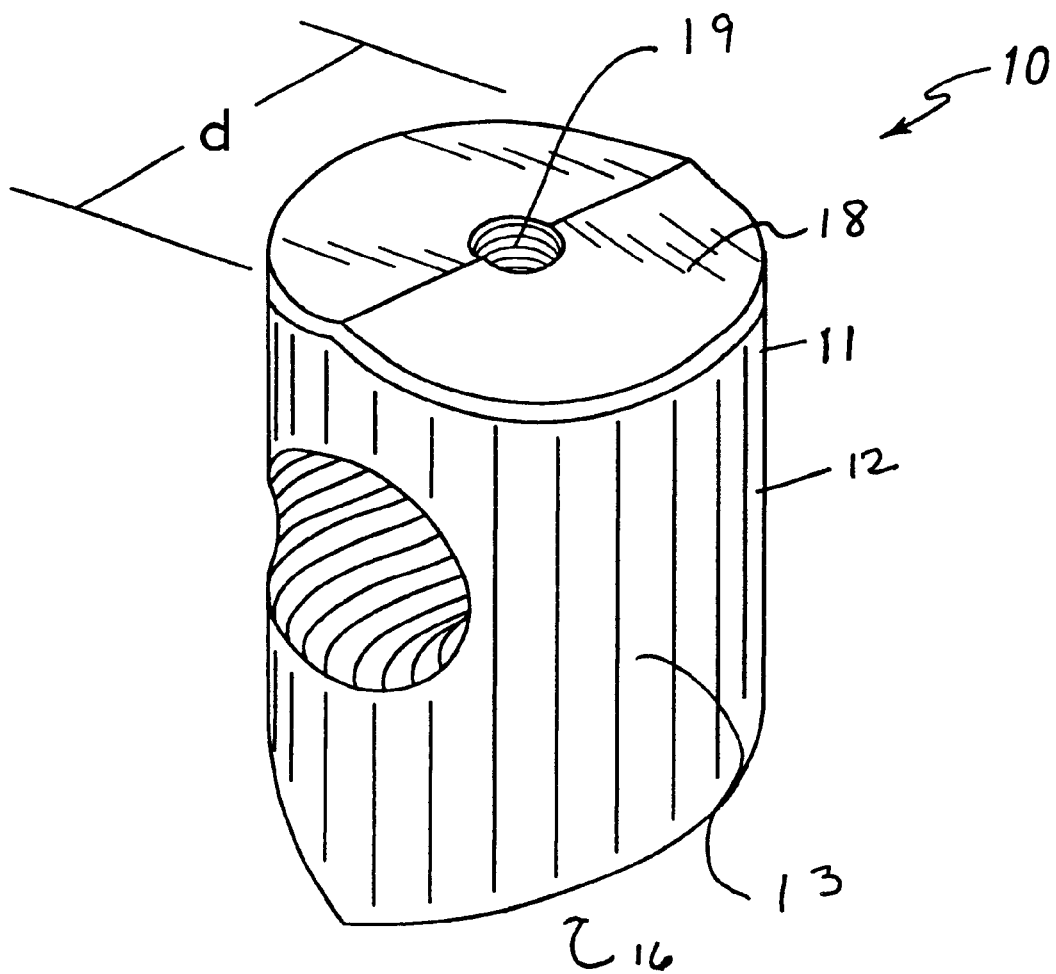
FIG. 1 is a top perspective view of a selectively deactivated bone BMP composite dowel according to this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated spacers, and such further applications of the principles of the invention as illustrated therein being contemplated as would normally occur to one skilled in the art to which the invention relates.

The present invention provides bone graft substitute compositions, spacers and surgical procedures. The bone graft compositions include selectively deactivated bone grafts in synergistic combination with an osteogenic material, such as a bone morphogenic protein (BMP). The bone grafts are selectively deactivated to remove all of the cellular material, fat and non-collagenous protein. In preferred embodiments, free collagen is also removed leaving structural or bound collagen which is associated with bone mineral to form the trabecular struts of bone. Although the graft is deproteinated and defatted, it still contains the natural crystalline structure of bone. Therefore, the deactivated bone of this invention has the natural micro-structure of bone without the risk of disease transmission or significant immunogenicity.

The natural crystalline structure of bone is maintained by the presence of structural collagen. This yields a selectively deactivated bone material with preferred physical characteristics. The presence of structural collagen and the natural mineral structure of bone results in an elasticity and radiopacity which is identical or nearly identical to bone. The material has sufficient resilience and elasticity to retain a formed body and yet remains rigid enough to maintain an open space between bone portions to result in a fusion mass. Other allograft materials such as demineralized bone matrix do not have the optimal physical properties to accomplish this without the assistance of a support.

When the selectively deactivated bone materials of this invention are combined with an osteogenic factor such as bone morphogenetic protein, the composite is an ideal bone graft substitute. The composite has the natural calcium phosphate structure of bone. This facilitates incorporation and substitution of the graft material giving the composites a desirable resorption rate of a few months. This compares favorably to the resorption rates of known materials which are typically either too fast, slow or unpredictable. For example, allograft typically is resorbed within 12–60 months but may, on the other hand, resorb too quickly before fusion can occur due to an immunogegenic response by the patient.

The combination of BMP and other osteogenic factors with a selectively deactivated bone graft according to this invention provides the osteoinductive potential of autograft without the need for a harvesting surgery. The osteoinductive composites of this invention enhance bone growth into and incorporation of the graft, resulting in fusion quicker than with graft alone. Allograft alone typically requires many months to incorporate and sometimes is never fully incorporated, but is merely encased within the patient's bone. The quicker fusion occuring within about five months provided by this invention compensates for the less desirable biomechanical properties of graft and makes the use of internal fixation and metal interbody fusion devices unnecessary. The spacers of this invention are not required to support the cyclic loads of the spine for very long because of the quick fusion rates which reduce the biomechanical demands on the spacer. However, when required the compositions of this invention may be used with internal fixation devices or may be reinforced as disclosed in copending application, A further advantage provided by this invention is that because the bone is selectively deactivated, the graft may be autogeneic, allogeneic or xenogeneic. The components of bone which could cause disease or prompt the patient's body to reject the graft are removed by the deactivation process. Xenogenic bone, such as bovine bone, is available in virtually unlimited supply. Several osteogenic factors are also available in unlimited supply thanks to recombinant DNA technology. Therefore, the present invention solves all of the problems associated with autograft, allograft and xenograft, including supply, immunogeneicity, disease transmission or additional surgeries.

This invention provides the further advantage of exploiting the discovery that bone mineral is an excellent carrier for osteogenic factors such as bone morphogenic proteins. Hydroxyapatite which is very similar in chemical composition to the mineral in cortical bone is an osteogenic factor-binding agent which controls the rate of delivery of certain proteins to the fusion site. Calcium phosphate compositions such as hydroxyapatite are thought to bind bone morphogenic proteins and prevent BMP from prematurely dissipating from the spacer before fusion can occur. It is further believed that retention of the BMP by the agent permits the protein to initiate the transformation of mesenchymal stem cells into bone producing cells or osteoblasts within the device at a rate that is conducive to complete and rapid bone formation and ultimately, fusion across the disc space. The spacers of this invention have the advantage of including a load bearing member composed of selectively deactivated bone which naturally binds and provides controlled delivery of osteogenic factors such as bone morphogenic proteins.

This invention also capitalizes on the discovery that cortical bone, like metal, can be conveniently machined into the various shapes disclosed herein. In some embodiments, the load bearing members define threads on an outer surface. Machined surfaces, such as threads, provide several advantages that were previously only available with metal implants. Threads allow better control of spacer insertion than can be obtained with a smooth surface. This allows the surgeon to more accurately position the spacer which is extremely important around the critical neurological and vascular structures of the spinal column. Threads and the like also provide increased surface area which facilitates the process of bone healing and creeping substitution for replacement of the donor bone material and fusion. These features also increase post-operative stability of the spacer by engaging the adjacent vertebral endplates and anchoring the spacer to prevent expulsion. This is a major advantage over smooth grafts. Surface features also stabilize the bone-spacer interface and reduce micromotion to facilitate incorporation and fusion.

The bone graft substitute compositions of this invention can be prepared according to conventional methods. Bone of human or animal source is obtained according to known procedures. The bone is cleaned to remove tissue and blood and is then treated with agents to remove cellular material, fats and noncollagenous proteins. Typical agents include alcohols and peroxides. In preferred embodiments, the bone material is also treated to remove free collagen, leaving bound or structural collagen. This reduces immunogenicity without compromising the structural integrity of the bone material. One preferred agent for removing free collagen and any remaining fat is sodium dodecyl sulfate (SDS). The deactivated bone material is then preferably washed with deionized water and sterilized by suitable methods.

The allograft dowel can be packaged fresh frozen or freeze dried, preferably freeze dried. Sterilization can be provided via aseptic processing or terminally sterilized by ETO, E-beam, or gamma irradiation preferably gamma irradiation. Gamma irradiation allows the procurement and processing of the allograft under less rigorous environmentally controlled conditions since terminal sterilization offers a significantly higher degree of sterility.

A preferred deactivated bone material is available from the University of Florida Tissue Bank, Inc. (UFTB) 1 Innovation Drive, Alachua, Fla. 32615, 904-462-3097 or 1-800-OAGRAFT. This material has been treated to remove all of the non-collagenous bone proteins leaving a non-immunogenic, disease-free, selectively deactivated bone product. This product has the natural mineral, microcrystalline structure of bone with a consistency which retains desired forms. The UFTB product is also preferred because it has a micro-structure which is the closest to natural bone of all of the known treated bone products. This bone product also has the radiopacity of natural bone and does not show the dense white image of the bone products of Spector and Geistlich. The UFTB product also provides superior resorbability, particularly when combined with an osteogenic factor. Resorption has been found to advantageously occur within several months as opposed to several years of the Spector and Geistlich materials or the few weeks of the Urist product. When the material is combined with a bone growth factor, the resorption time is ample for forming the boney bridge required for fusion and bone healing. The UFTB material also has an elasticity similar to normal bone while the Spector and Geistlich materials have been found to be brittle and weak.

The bone materials of this invention are preferably synergistically combined with an osteogenic composition or material containing a bone growth factor or protein. An osteogenic material can be applied to the bone material by impregnating the graft with a solution including an osteogenic composition. The allograft is allowed to soak for sufficient enough time to allow the allograft to absorb the protein. Additional protein could be used with the allograft by the incorporation of the protein of a delivery vehicle and placed around or in the allograft. In some embodiments, an osteogenic composition can be packed into a chamber defined within a body of the material. The composition may be applied by the surgeon during surgery or the spacer may be supplied with the composition preapplied. In such cases, the osteogenic composition may be stabilized for transport and storage such as by freeze-drying. The stabilized composition can be rehydrated and/or reactivated with a sterile fluid such as saline or water or with body fluids applied before or after implantation. The term osteogenic composition used here means virtually any material that promotes bone growth or healing including natural, synthetic and recombinant proteins, hormones and the like.

The osteogenic compositions used in this invention preferably comprise a therapeutically effective amount to stimulate or induce bone growth or healing of a substantially pure bone inductive factor such as a bone morphogenetic protein in a pharmaceutically acceptable carrier. The preferred osteoinductive factors include, but are not limited to, the recombinant human bone morphogenic proteins (rhBMPs) because they are available in unlimited supply and do not transmit infectious diseases. Most preferably, the bone morphogenetic protein is a rhBMP-2, rhBMP-4 or heterodimers thereof. The concentration of rhBMP-2 is generally between about 0.4 mg/ml to about 1.5 mg/ml, preferably near 1.5 mg/ml. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat.

Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenic protein from bone are described in U.S. Pat. No. 4,294,753 to Urist and Urist et al., 81 PNAS 371, 1984.

The choice of carrier material for the osteogenic composition is based on the application desired, biocompatibility, biodegradability, and interface properties. The bone growth inducing composition can be introduced into the pores of the bone material in any suitable manner. For example, the composition may be injected into the pores of the graft. In other embodiments, the composition is dripped onto the graft or the graft is soaked in or sprayed with a solution containing an effective amount of the composition to stimulate osteoinduction. In either case the pores are exposed to the composition for a period of time sufficient to allow the liquid to throughly soak the graft. The osteogenic factor, preferably a BMP, may be provided in freeze-dried form and reconstituted in a pharmaceutically acceptable liquid or gel carrier such as sterile water, physiological saline or any other suitable carrier. The carrier may be any suitable medium capable of delivering the proteins to the spacer. Preferably the medium is supplemented with a buffer solution as is known in the art. In one specific embodiment of the invention, rhBMP-2 is suspended or admixed in a carrier, such as water, saline, liquid collagen or injectable bicalcium phosphate. In a most preferred embodiment, BMP is applied to the pores of the graft and then lypholized or freeze-dried. The graft-BMP composition can then be frozen for storage and transport Alternatively, the osteoinductive protein can be added at the time of surgery.

Other osteoinductive protein carriers are available to deliver proteins to a chamber defined within the bone material or to locations around the implantation site of the bone material. Potential carriers include calcium sulphates, polylactic acids, polyanhydrides, collagen, calcium phosphates, polymeric acrylic esters and demineralized bone. The carrier may be any suitable carrier capable of delivering the proteins. Most preferably, the carrier is capable of being eventually resorbed into the body. One preferred carrier is an absorbable collagen sponge marketed by Integra LifeSciences Corporation under the trade name Helistat® Absorbable Collagen Hemostatic Agent. Another preferred carrier is an open cell polylactic acid polymer (OPLA). Other potential matrices for the compositions may be biodegradable and chemically defined calcium sulfates, calcium phosphates such as tricalcium phosphate (TCP) and hydroxyapatite (HA) and including injectable bicalcium phosphates (BCP), and polyanhydrides. Other potential materials are biodegradable and biologically derived, such as bone or dermal collagen. Further matrices are comprised of pure proteins or extracellular matrix components. The osteoinductive material may also be an admixture of BMP and a polymeric acrylic ester carrier, such as polymethylmethacrylic.

For packing the chambers of the spacers of the present invention, the carriers are preferably provided as a sponge which can be compressed into the chamber or as strips or sheets which may be folded to conform to the chamber. Preferably, the carrier has a width and length which are each slightly greater than the width and length of the chamber. In the most preferred embodiments, the carrier is soaked with a rhBMP-2 solution and then compressed into the chamber. The sponge is held within the chamber by the compressive forces provided by the sponge against the wall of the dowel. It may be preferable for the carrier to extend out of the openings of the chamber to facilitate contact of the osteogenic composition with the highly vascularized tissue surrounding the fusion site. The carrier can also be provided in several strips sized to fit within the chamber. The strips can be placed one against another to fill the interior. As with the folded sheet, the strips can be arranged within the spacer in several orientations. Preferably, the osteogenic material, whether provided in a sponge, a single folded sheet or in several overlapping strips, has a length corresponding to the length and width of the chamber.

The most preferred carrier is a biphasic calcium phosphate ceramic. Hydroxyapatite/tricalcium phosphate ceramics are preferred because of their desirable bioactive properties and degradation rates in vivo. The preferred ratio of hydroxyapatite to tricalcium phosphate is between about 0:100 and about 65:35. Any size or shape ceramic carrier which will fit into the chambers defined in the load bearing member are contemplated. Ceramic blocks are commercially available from Sofamor Danek Group, B. P. 4-62180 Rang-du-Fliers, France and Bioland, 132 Route d:Espagne, 31100 Toulouse, France. Of course, rectangular and other suitable shapes are contemplated. The osteoinductive factor is introduced into the carrier in any suitable manner. For example, the carrier may be soaked in a solution containing the factor.

The present invention also provides spacers for maintaining a space between adjacent bones. The spacers include a body composed of a selectively deactivated bone graft in synergistic combination with a bone growth factor. The bone source is any suitable bone material preferably of any vertebrae origin, including tibial, fibial, humeral, iliac, etc. The bodies of this invention include flat spacers, bone dowels, cortical rings, bone chips and any other suitably shaped bone piece. A preferred body is obtained from the diaphysis of a long bone having a medullary canal which forms a natural chamber in the graft.

In one specific embodiment depicted in FIG. 1, the invention provides a spacer 10 for maintaining a space between adjacent bone in a patient. The spacer 10 includes a load bearing member or body 11 sized and shaped to fit within the space. The body 11 is preferably composed of a natural selectively deactivated bone material which has been processed to remove associated non-collagenous bone proteins. The bone material contains native collagen materials and naturally associated bone minerals but is substantially free from native non-collagenous protein. The chemical composition of the bone material allows it to resiliently retain a shaped body. The shape of the body is preferably formed, and the body machined to have desired surface features, before the bone material is deactivated. However, in some embodiments a mass of bone is deactivated and then is shaped or machined to form a particular body.

Figure 2:
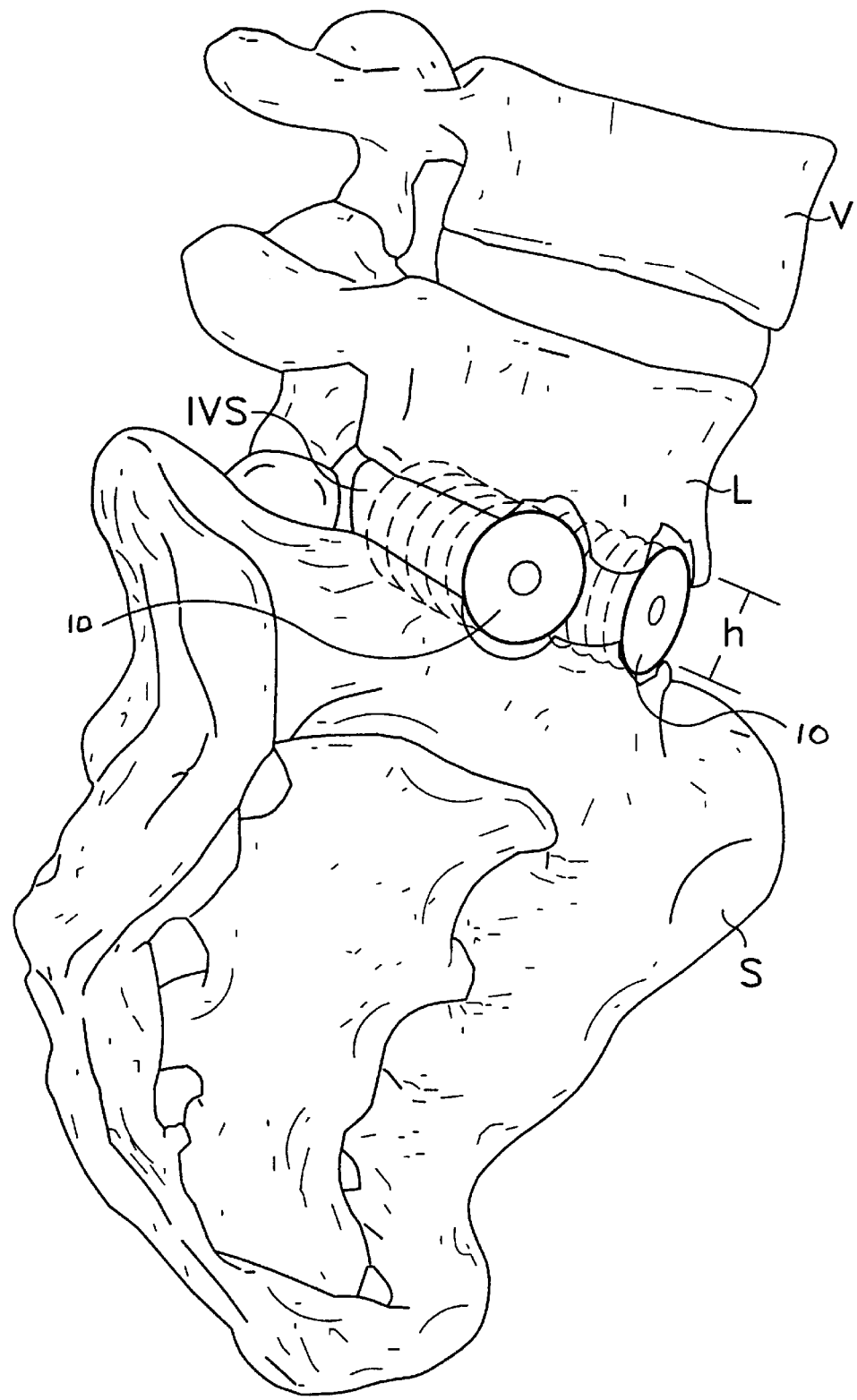
FIG. 2 shows bilateral dowel placement between L5 and the sacrum.

Referring now to FIGS. 1 and 2, in some embodiments, the body 11 is shaped as a dowel. Dowel shaped bodies are sometimes preferred when the bones are vertebrae to be fused. The dowel 10 includes a wall 12 sized for engagement within the intervertebral space IVS to maintain the space IVS. The wall 12 defines an outer engaging surface 13 for contacting the adjacent vertebrae. The wall 12 is preferably cylindrically so that the bone dowel 10 has a diameter d which is larger than the height h of the space IVS between adjacent vertebrae V or the height of the space between the lowest lumbar vertebrae L5 and the sacrum S as depicted in FIG. 2.

Figure 3:
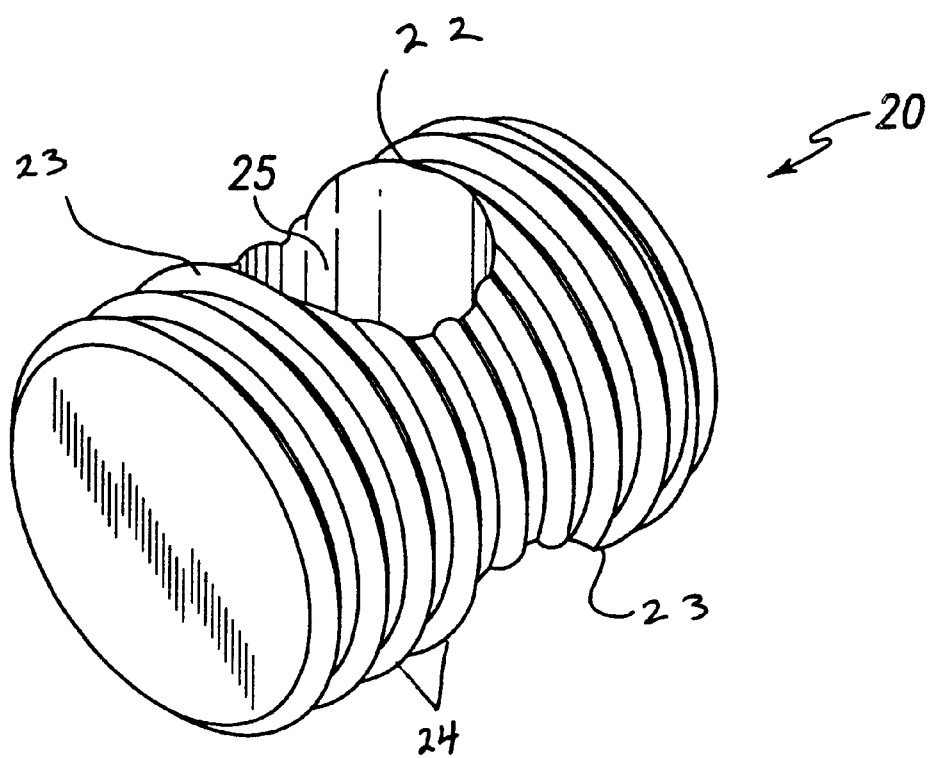
FIG. 3 is a perspective view of a cortical dowel having a chamber.
Figure 4:
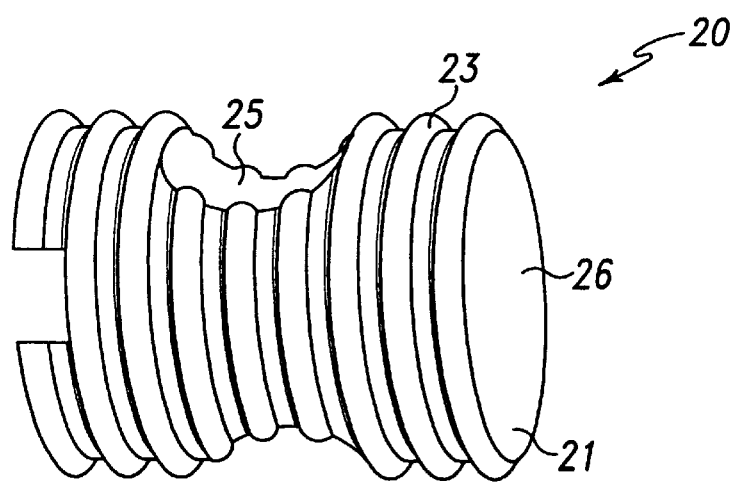
FIG. 4 is a side perspective view of a dowel according to this invention.
Figure 5:
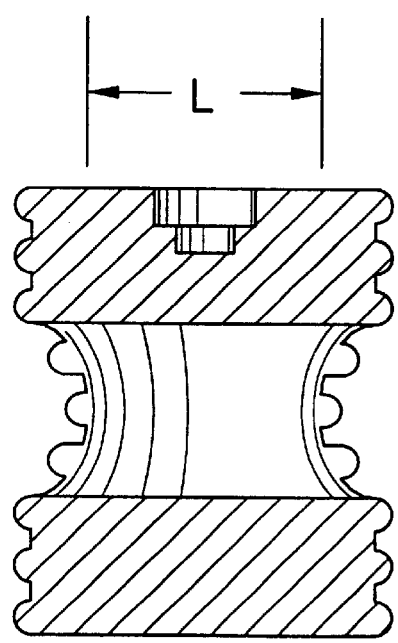
FIG. 5 is a cross-section of another dowel of this invention.
Figure 6:
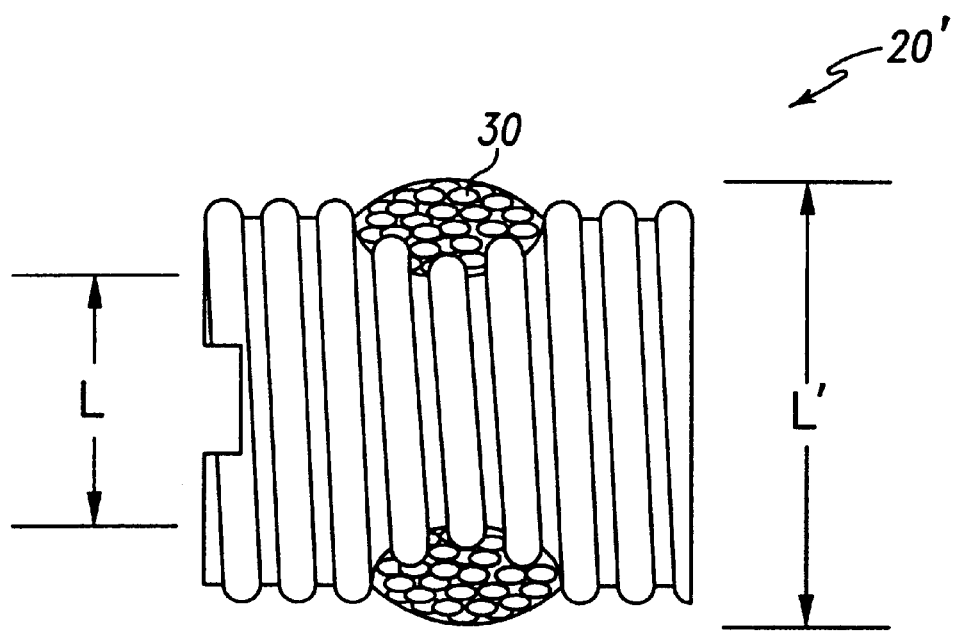
FIG. 6 is a side elevational view of the dowel shown in FIG. 5.

In another embodiment depicted in FIG. 3, the body is a bone dowel 20 which includes a wall 22 having an engagement surface 23. The wall 22 defines a chamber 25 therethrough. Preferably, the load bearing member is a bone graft obtained from the diaphysis of a long bone having a medullary canal which forms the chamber 25. Such dowels are available from the UFTB. The chamber 25 can be packed with an osteogenic composition to stimulate osteoinduction. The chamber 25 is preferably defined through a pair of outer engaging surfaces 23 so that the composition has maximum contact with the endplates of the adjacent vertebrae. Referring now to FIG. 4, the spacer 20 preferably includes a solid protective wall 26 which is positionable to protect the spinal cord from escape or leakage of material packed within the chamber 25. In anterior approaches, the protective wall 26 is posterior. Preferably, the osteogenic composition has a length which is greater than the length of the chamber (FIGS. 5 and 6) and the composition is disposed within the chamber 25 to contact the end plates of adjacent vertebrae when the spacer 20' is implanted between the vertebrae. This provides better contact of the composition with the end plates to stimulate osteoinduction.

Various features can be machined on the outer surfaces of the dowels of this invention. In one embodiment shown in FIG. 3, the dowel 20 includes an outer engaging surface 23 defining threads 24. Referring again to FIG. 1, in some embodiments, the dowel 10 is provided with a tool engaging hole 19 in a wall 18 opposite the solid protective wall 16. The tool engaging hole 19 is provided in a surface of the dowel which is adjacent the surgeon and opposite the initial thread 17. For an anterior procedure, the tool engaging tool hole 19 would be provided in the anterior surface of the dowel 10. Other machined features are contemplated in the outer or bone engaging surfaces 23. Such machine features include surface roughenings such as knurlings and ratchetings.

The spacers of this invention can be inserted using conventional techniques and known tools. In accordance with additional aspects of the present invention, methods for implanting an interbody fusion spacer, such as the spacer 40, are contemplated. These methods are also disclosed in commonly assigned, co-pending U.S. patent application Ser. No. 08/604,874, METHODS AND INSTRUMENTS FOR INTERBODY FUSION. The spacers of this invention can also be inserted using laproscopic technology as described in Sofamor Danek USA's *Laproscopic Bone Dowel Surgical Technique,*© 1995, 1800 Pyramid Place, Memphis, Tenn. 38132, 1-800-933-2635. Devices of this invention can be conveniently incorporated into Sofamor Danek's laproscopic bone dowel system that facilitates anterior interbody fusions with an approach that is much less surgical morbid than the standard open anterior retroperitoneal approaches. This system includes templates, trephines, dilators, reamers, ports and other devices required for laproscopic dowel insertion.

The body may also include other shapes such as cortical rings as shown in FIG. 7. Such cortical rings 50 are obtained by a cross-sectional slice of the diaphysis of a long bone and include superior surface 51 and inferior surface 52. The graft shown in FIG. 7 includes an outer surface 53 which is adjacent and between the superior 51 and inferior 52 surfaces. In one embodiment bone growth thru-holes 53a are defined through the outer surface 53 to facilitate fusion. The holes 53a allows mesenchymal stem cells to creep in and bone growth protein to diffuse out of the graft. This facilitates bone graft incorporation and possibly accelerates fusion by forming anterior and lateral bone bridging outside and through the device. In another embodiment the outer surface 53 defines a tool engaging hole 54 for receiving an implanting tool. In a preferred embodiment, at least one of the superior and/or inferior surfaces 51,52 are roughened for gripping the end plates of the adjacent vertebrae. The surface roughenings may include teeth 56 on ring 50' as shown in FIG. 8 or waffle pattern 57 as shown on ring 50" in FIG. 9. When cortical rings are used as the graft material the ring 50 may be trimmed for a more uniform geometry as shown in FIG. 7 or left in place as shown in FIG. 9.

The graft can also be formed into a square shape to be conveniently incorporated into current surgical procedures such as, the Smith-Robinson technique for cervical fusion (Smith, M. D., G. W. and R. A. Robinson, M. D., "The Treatment of Certain Cervical-Spine Disorders By Anterior Removal Of The Intervertebral Disc And Interbody Fusion", *J. Bone And Joint Surgery,* 40-A:607–624 (1958) and Cloward, M. D., R. B., "The Anterior Approach For Removal Of Ruptured Cervical Disks", in meeting of the Harvey Cushing Society, Washington, D.C., Apr. 22, 1958). In such procedures, the surgeon prepares the endplates of the adjacent vertebral bodies to accept a graft after the disc has been removed. The endplates are generally prepared to be parallel surfaces with a high speed burr. The surgeon then typically sculpts the graft to fit tightly between the bone surfaces so that the graft is held by compression between the vertebral bodies. The bone graft is intended to provide structural support and promote bone ingrowth to achieve a solid fusion of the affected joint. The spacers of this invention avoid the need for this graft sculpting as spacers of known size and dimensions are provided. This invention also avoids the need for a donor surgery because the osteoinductive properties of autograft are not required. The spacers can be combined with osteoinductive materials that make allograft osteoinductive. Therefore, the spacers of this invention speed the patient's recovery by reducing surgical time, avoiding a painful donor surgery and inducing quicker fusion.

The following specific examples are provided for purposes of illustrating the invention, and no limitations on the invention are intended thereby.

EXAMPLE 1

PREPARATION OF DIAPHYSIAL CORTICAL BONE DOWEL

A consenting donor (i.e., donor card or other form of acceptance to serve as a donor) was screened for a wide variety of communicable diseases and pathogens, including human immunodeficiency virus, cytomegalovirus, hepatitis B, hepatitis C and several other pathogens. These tests may be conducted by any of a number of means conventional in the art, including but not limited to ELISA assays, PCR assays, or hemagglutination. Such testing follows the requirements of: (i) American Association of Tissue Banks, Technical Manual for Tissue Banking, Technical Manual—Musculoskeletal Tissues, pages M19–M20; (ii) The Food and Drug Administration, Interim Rule, Federal Register/Vol. 50, No. 238/Tuesday, Dec. 14, 1993/Rules and Regulations/65517, D. Infectious Disease Testing and Donor Screening, (iii) MMWR/Vol. 43/No. RR-8, Guidelines for Preventing Transmission of Human Immunodeficiency Virus Through Transplantation of Human Tissue and Organs, pages 4–7; (iv) Florida Administrative Weekly, Vol. 10, No. 34, Aug. 21, 1992, 59A-1.001-014 59A-1.005(12) (c), F.A.C., (12)(a)–(h), 59A-1.005(15), F.A.C., (4)(a)–(8). In addition to a battery of standard biochemical assays, the donor, or their next of kin, was interviewed to ascertain whether the donor engaged in any of a number of high risk behaviors such as having multiple sexual partners, suffering from hemophilia, engaging in intravenous drug use etc. After the donor was ascertained to be acceptable, the bones useful for obtention of the dowels were recovered and cleaned.

A dowel was obtained as a transverse plug from the diaphysis of a long bone using a diamond tipped cutting bit which was water cleaned and cooled. The bit was commercially available (Starlite, Inc) and had a generally circular nature and an internal vacant diameter between about 10 mm to about 20 mm. The machine for obtention of endo- and cortical dowels consisted of a pneumatic driven miniature lathe which is fabricated from stainless steel and anodized aluminum. It has a spring loaded carriage which travels parallel to the cutter. The carriage rides on two runners which are 1.0 inch stainless rods and has a travel distance of approximately 8.0 inches. One runner has set pin holes on the running rod which will stop the carriage from moving when the set pin is placed into the desired hole. The carriage is moveable from side to side with a knob which has graduations in metric and in English. This allows the graft to be positioned. On this carriage is a vice which clamps the graft and holds it in place while the dowel is being cut. The vice has a cut out area in the jaws to allow clearance for the cutter. The lathe has a drive system which is a pneumatic motor with a valve controller which allows a desired RPM to be set.

First, the carriage is manually pulled back and locked in place with a set pin. Second, the graft is loaded into the vice and is aligned with the cutter. Third, the machine is started and the RPM is set, by using a knob on the valve control. Fourth, the set pin, which allows the graft to be loaded onto the cutter to cut the dowel. Once the cutter has cut all the way through the graft the carriage will stop on a set pin. Fifth, sterile water is used to eject dowel out of the cutter. It is fully autoclavable and has a stainless steel vice and/or clamping fixture to hold grafts for cutting dowels. The graft can be positioned to within 0.001" of an inch which creates dowel uniformity during the cutting process.

The cutter used in conjunction with the above machine can produce dowels ranging from 5 mm to 30 mm diameters and the sizes of the cutters are 10.6 mm; 11.0 mm; 12.0 mm; 13.0 mm; 14.0 mm; 16.0 mm; and 18.0 mm. The composition of the cutters is stainless steel with a diamond powder cutting surface which produces a very smooth surface on the wall of the dowels. In addition, sterile water is used to cool and remove debris from graft and/or dowel as the dowel is being cut (hydro infusion). The water travels down through the center of the cutter to irrigate as well as clean the dowel under pressure. In addition, the water aides in ejecting the dowel from the cutter.

The marrow was then removed from the medullary canal of the dowel and the cavity cleaned to create of chamber. The final machined product may be stored, frozen or freeze-dried and vacuum sealed for later use.

EXAMPLE 2

THREADING DOWELS

A diaphysial cortical bone dowel is prepared as described above. The plug is then machined, preferably in a class 10 clean room, to the dimensions desired. The machining is preferably conducted on a lathe such as a jeweler's lathe or machining tools may be specifically designed and adapted for this purpose. A hole is then drilled through the anterior wall of the dowel. The hole is then tapped to receive a threaded insertion tool.

EXAMPLE 3

PREPARATION OF DEACTIVATED ALLOGRAFT

Allograft was procured using standard accepted practices according to Example 1. Under clean room conditions, the graft was cut up into desired final physical shape and size, into cylindrical cortical bone dowels. The allograft was then chemically treated to enzymatically dissolve and remove all cellular and non-collagenous proteinaceous material to reduce immunogenicity and risk of disease transmission. The graft was soaked in isopropyl alcohol to dissolve fat. The graft was then soaked in peroxide to remove non-collagenous proteins and fat. The deproteinated and defatted graft was then exposed to SDS to remove free collagen and any remaining fat, leaving structural collagen. The deactivated graft was then washed with deionized water to rinse processing chemicals and debris. Gamma irradiation terminal sterilization was then employed. The resulting allograft primarily consisted of structural collagen and natural bone mineral.

EXAMPLE 4

PREPARATION OF DEACTIVATED BONE DOWEL-rhBMP-2 COMPOSITE BY DRIPPING

A threaded deactivated dowel is obtained through the methods of Examples 1 and 2.

A vial containing 4.0 mg of lypholized rhBMP-2 (Genetics Institute) is constituted with 1 mL sterile water (Abbott Laboratories) for injection to obtain a 4.0 mg/mL solution as follows:

1. Using a 3-cc syringe and 22G needle, slowly inject 1.0 mL sterile water for injection into the vial containing lypholized rhBMP-2.
2. Gently swirl the vial until a clear solution is obtained. Do not shake.

The dilution scheme below is followed to obtain the appropriate rhBMP-2 concentration. This dilution provides sufficient volume for two dowels. The dilutions are performed as follows:

1. Using a 5-cc syringe, transfer 4.0 mL of MFR 906 buffer (Genetics Institute) into a sterile vial.
2. Using a 1-cc syringe, transfer 0.70 mL reconstituted rhBMP-2 into the vial containing the buffer.
3. Gently swirl to mix.

| DILUTION SCHEME | | | |
| --- | --- | --- | --- |
| INITIAL rhBMP-2 CONCENTRATION (mg/mL) | rhBMP-2 VOLUME (mL) | MFR-842 VOLUME (mL) | FINAL rhBMP-2 CONCENTRATION (mg/mL) |
| 4.0 | 0.7 | 4.0 | 0.60 |

1. Using a 3-cc syringe and 22G needle, slowly drip 2.0 mL of 0.60 mg/mL rhBMP-2 solution onto the Bone Dowel.
2. Implant immediately.

EXAMPLE 5

PREPARATION OF DEACTIVATED ALLOGRAFT BONE BMP COMPOSITE BY SOAKING

1. Freeze dried rhBMP-2 is reconstituted with sterile water for injection as in Example A.

2. A sterile allograft bone dowel is transferred to a sterile "soaking" container.
3. Reconstituted rhBMP-2 is added to the soaking container so that the allograft is completely submersed in a BMP solution.
4. The allograft bone dowel is allowed to soak in the rhBMP-2 solution for 30–60 minutes so that the graft absorbs the protein.

EXAMPLE 6

BONE DOWEL PACKED WITH BMP-2/ COLLAGEN COMPOSITION

A threaded deactivated dowel is obtained through the methods of Examples 1–3.

A vial containing 4.0 mg of lypholized rhBMP-2 (Genetics Institute) is constituted with 1 mL sterile water (Abbott Laboratories) for injection to obtain a 4.0 mg/mL solution as follows:

1. Using a 3-cc syringe and 22G needle, slowly inject 1.0 mL sterile water for injection into the vial containing lypholized rhBMP-2.
2. Gently swirl the vial until a clear solution is obtained. Do not shake.

The dilution scheme below is followed to obtain the appropriate rhBMP-2 concentration. The dilutions are performed as follows:

1. Using a 3-cc syringe, transfer 2.5 mL of MFR-842 buffer (Genetics Institute) into a sterile vial.
2. Using a 1-cc syringe, transfer 0.30 mL of 4.0 mg/mL reconstituted rhBMP-2 into the vial containing the buffer.
3. Gently swirl to mix.

| DILUTION SCHEME | | | |
| --- | --- | --- | --- |
| INITIAL rhBMP-2 CONCENTRATION (mg/mL) | rhBMP-2 VOLUME (mL) | MFR-842 VOLUME (mL) | FINAL rhBMP-2 CONCENTRATION (mg/mL) |
| 4.0 | 0.3 | 2.5 | 0.43 |

The rhBMP-2 solution is applied to a Helistat sponge (Genetics Institute) as follows:

1. Using sterile forceps and scissors, cut a 7.5 cm×2.0 cm strip of Helistat off of a 7.5×10 cm (3"×4") sponge.
2. Using a 1-cc syringe with a 22-G needle, slowly drip approximately 0.8 mL of 0.43 mg/mL rhBMP-2 solution uniformly onto the Helistat sheet.
3. Using sterile forceps, loosely pack the sponge into the chamber of the dowel.
4. Using a 1-cc syringe with a 22-G needle, inject the remaining 0.8 mL of 0.43 mg/mL rhBMP-2 into the sponge in the dowel through the openings of the chamber.
5. Implant immediately.

EXAMPLE 7

BONE DOWEL PACKED rhBMP-2/HA/TCP COMPOSITION

A threaded deactivated dowel is obtained through the methods of Examples 1–3.

A vial containing 4.0 mg of lypholized rhBMP-2 (Genetics Institute) is constituted with 1 mL sterile water (Abbott Laboratories) for injection to obtain a 4.0 mg/mL solution as follows:

1. Using a 3-cc syringe and 22G needle, slowly inject 1.0 mL sterile water for injection into the vial containing lypholized rhBMP-2.
2. Gently swirl the vial until a clear solution is obtained. Do not shake.

A cylindrical block of biphasic hydroxyapatite/tricalcium phosphate (Bioland) is wetted with a 0.4 mg/mL rhBMP-2 solution. The BMP-ceramic block is packed into the chamber of the dowel and the dowel is then implanted.

EXAMPLE 8

DEACTIVATED ALLOGRAFT BONE CHIP-COMPOSITE PREPARATION

1. Allograft chips are harvested, processed and prepared according to Examples 1 and 2.
2. Freeze dried rhBMP-2 is reconstituted with sterile water for injection as described in Example 4.
3. The sterile cancellous allograft bone chips are transferred to the sterile "soaking" container.
4. Reconstituted rhBMP-2 is placed into the soaking container so that the allograft is completely submersed.
5. The allograft bone chips are soaked in the rhBMP-2 solution for 30–60 minutes.
6. Using sterile forceps, the allograft bone chips are removed from the soaking container and placed into the posterolateral gutters of the level of the spine to be fused.

EXAMPLE 9

PREPARATION OF DEACTIVATED CORTICAL RING-COMPOSITES

A selectively deactivated cortical ring is obtained as a cross-sectional slice of the diaphysis of a human long bone and then prepared using the methods described in Examples 1–3. The ring is fashioned into a square hollow ring. The ring is packed with an osteogenic composition as described in

EXAMPLE 6 or 7.

EXAMPLE 10

SPACERS

A deactivated D-shaped cervical spacer is obtained as a cross-sectional slice of a diaphysis of a long bone and then prepared using the methods of Examples 1–3. The exterior surfaces of the walls are formed by machining the slice to a D-shape. The engaging surfaces of the spacer are provided with knurlings by a standard milling machine. A hole is then drilled through the anterior wall of the spacer. The hole is then tapped to engage a threaded insertion tool. The chamber of the spacer is then packed with an osteogenic composition as described in EXAMPLE 6 or 7.

EXAMPLE 11

ANTEROR INTERBODY CERVICAL FUSION

The cervical spine is approached anteriorly according to known surgical techniques. The composite material is placed within the interdiscal space.

EXAMPLE 12

POSTEROLATERAL FUSION

The spine is approached posterolaterially according to known surgical techniques. The composite material of Example 4 is placed between portions of adjacent vertebrae.

EXAMPLE 13

USE OF COMPOSITE WITH BINDING MATRIX

Processed allograft according to Example 8 is added to a binding matrix to hold the allograft chips together improving their handling characteristics. The allograft chips are added to a types I bovine collagen slurry and then freeze dried into a sheet form. At the time of surgery the surgeon hydrates the collagen/allograft composite sponge with an osteoinductive protein solution. Alternatively, the protein solution could be freeze dried on the sponge during manufacture of the sponge. Alternative binding matrix materials include gelatin, glycvosaminoglycans, hyluonic acid, polymers, proteins and other suitable materials.

EXAMPLE 14

The processing methods and chemical and physical properties are studied for the composite of Examples 1 and 2 and the materials disclosed in U.S. Pat. No. 5,573,771 to Geistlich et al., U.S. Pat. No. 4,882,149 to Spector and Urist, "A Chemosterilized Antigen-Extracted Autodigested Alloimplant for Bone Banks", Urist et al. using known methods. The results are compared in Tables I–III below.

CONCLUSION

The combination of a bone growth factor with a deactivated bone graft provides superior results. Quicker fusion rates provide enhanced mechanical strength sooner. The deactivated bone of this invention is an excellent protein carrier which provides controlled release of BMP to the fusion site. The presence of structural collagen and the natural mineral structure of bone results in an elasticity and radiopacity which is identical or nearly identical to bone. The material has sufficient resilience and elasticity to retain a formed body and yet remains rigid enough to maintain an open space between bone portions to result in a fusion mass.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

TABLE I

PROCESSING CHARACTERISTICS

| | Material | Processing | Final Product | Contents |
|---|---|---|---|---|
| Spector/ Geistlich | Processed Bone Mineral | Extractions High Temp. Step (300° C.) Terminal Sterilization | Mineral Scaffold | Mineral |
| Urist | Antigen Extracted Allograft (AAA bone) | Extractions Demineralization | Aseptic Processed Allograft Particles | Some Mineral Collagen Proteins |

TABLE I-continued

PROCESSING CHARACTERISTICS

| | Material | Processing | Final Product | Contents |
|---|---|---|---|---|
| McKay | Deproteinated/ Deactivated Bone | Extractions Terminal Sterilization | Sterile Processed Allograft Scaffold | Mineral Collagen |

TABLE II

CHEMICAL PROPERTIES

| | Organic Material | Presence of BMP | Osteoinductivity | Resorbability |
|---|---|---|---|---|
| Spector/ Geistlich | No | No | No | Poor (>5 years) |
| Urist | Yes | Yes | Yes | Very Fast (weeks) |
| McKay | Yes | No | No | Fast (months) |

TABLE III

PHYSICAL PROPERTIES

| | Form | Strength | Appearance on X-ray | Accessibility of New Bone Radiographically |
|---|---|---|---|---|
| Spector/ Geistlich | Scaffold | Brittle/Friable/ Weak | Denser than normal bone (white) | Poor |
| Urist | Particles | Weaker than than normal | Less dense normal bone (radiolucent) | Good |
| McKay | Scaffold | Elastic - similar to normal bone | Similar to normal bone (slight radiopacity) | Good |

What is claimed is:

1. A spacer for maintaining a space between a pair of adjacent vertebrae in a spine, comprising:
   a body sized and shaped to fit in said space, said body composed of a natural selectively deactivated bone material containing native collagen materials and naturally-associated bone minerals, said body having been processed to remove associated non-collagenous bone proteins; and
   a therapeutically-effective amount to stimulate bone growth of a bone growth factor in a pharmaceutically-acceptable carrier in synergistic combination with said bone material.

2. The spacer of claim 1 wherein said body defines a superior wall for contacting one of the vertebrae, an inferior wall for contacting the other vertebrae and a lateral wall adjacent and between said superior wall and said inferior wall, said lateral wall defining a thru hole.

3. The spacer of claim 1 wherein said body comprises a femoral ring.

4. The spacer of claim 1 wherein said body comprises a bone dowel.

5. The spacer of claim 1 wherein said walls define a chamber and said carrier is packed within said chamber.

6. The spacer of claim 1 wherein said carrier is dispersed within said material.

7. The spacer of claim 1 wherein said body is fully resorbable after implantation no later than about five months.

8. The spacer of claim 1 wherein said body has approximately the radiopacity after implantation of the bones of the vertebrate.

9. The spacer of claim 1 wherein said bone graft is bovine bone.

10. The spacer of claim 1, wherein said bone material is sterilized by irradiation prior to combination with said bone growth factor.

11. A spacer for maintaining a space between a pair of adjacent vertebrae and a spine, comprising:

a body sized and shaped to fit in said space, said body composed of a natural selectively deactivated bone material containing native collagen materials and naturally-associated bone minerals, said body having been processed to remove associated fats and non-collagenous bone proteins; and a therapeutically-effective amount to stimulate bone growth of a bone growth factor in a pharmaceutically-acceptable carrier dispersed within said bone material.

12. The spacer of claim 11, wherein said body comprises a femoral ring.

13. The spacer of claim 11 wherein said body comprises a bone dowel.

14. A method for preparing a spacer for maintaining a space between a pair of adjacent vertebrae and a spine, comprising:

providing a body sized and shaped to fit in said space, said body composed of a natural selectively deactivated bone material containing native collagen materials and naturally-associated bone minerals, said body having been processed to remove fats and associated non-collagenous bone proteins;

subjecting said body to radiation sufficiently to sterilize said bone material; and combining said body with a therapeutically-effective amount to stimulate bone growth of a bone growth factor in a pharmaceutically-acceptable carrier.

* * * * *